United States Patent [19]

Tyman

[11] Patent Number: 4,697,038
[45] Date of Patent: Sep. 29, 1987

[54] METAL EXTRACTION USING A NOVEL GROUP OF COMPOUNDS AND CHEMICAL PURIFICATION METHOD

[75] Inventor: John H. P. Tyman, London, England

[73] Assignee: 501 Brunel University, Middlesex, England

[21] Appl. No.: 587,068

[22] Filed: Mar. 7, 1984

[30] Foreign Application Priority Data

Oct. 24, 1983 [GB] United Kingdom ............... 8328403

[51] Int. Cl.$^4$ ................................. C07C 131/00
[52] U.S. Cl. ........................................... 564/265
[58] Field of Search ........................... 564/265, 266

[56] References Cited

U.S. PATENT DOCUMENTS 3,592,775  7/1971  Swanson ........................... 564/266
3,939,203  2/1976  Mattison et al. ................... 564/266
4,020,105  4/1977  Ackerley et al. .................. 564/265

FOREIGN PATENT DOCUMENTS 2104516  3/1983  United Kingdom ............... 564/266

OTHER PUBLICATIONS

Beswick, Geoffrey Ernest *Chemical Abstracts* vol. 87 (1977) #102,066q.
Dalton, Raymond Frederick *Chemical Abstracts* vol. 89 (1978) #9650g.

*Primary Examiner*—Natalie Trousof
*Assistant Examiner*—L. Hendriksen
*Attorney, Agent, or Firm*—Birch, Stewart, Kolasch & Birch

[57] ABSTRACT

Compounds of the formula

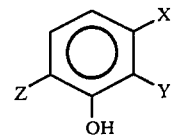

in which;
  X represents a straight chain hydrocarbyl group containing from 8 to 17 carbon atoms;
  Y represents H or the group—CH=NOH, and
  Z represents H or the group—CH=NOH or the group—CPh=NOH, provided that at least one of Y and Z represents H; or such compound containing at least one electronegative substituent in the aromatic ring, may be prepared from anacardic acid and its analogues, and are useful for the extraction of copper from acidic aqueous solution. Cardanol, which has the formula

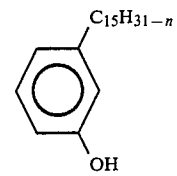

where n=0, 2, 4 or 6 is recovered from cashew nut shell liquid containing cardol and other dihydric phenols by reacting the dihydric phenols in the CNSL with an aldehyde while leaving the cardanol substantially unreacted, and vacuum distilling the cardanol from the reaction mixture.

8 Claims, No Drawings

METAL EXTRACTION USING A NOVEL GROUP OF COMPOUNDS AND CHEMICAL PURIFICATION METHOD

The present invention relates to a novel group of chemical compounds, and to method of using the novel compounds in a metal extraction process. There has also been devised a method of purifying mixtures containing certain of the novel compounds, which forms a part of this invention.

The compound (2-hydroxy 5-tertiary nonyl-)acetophenone oxime which is commercially available in a hydrocarbon diluent, is useful for the extraction of copper from acidic media but is at present derived from petroleum, the supply and price of which is liable to fluctuation.

Compounds have now been found which can extract relatively greater amounts of copper from acidic media and which can be produced from the replenishable source Cashew Nut-Shell Liquid (CNSL) and from related Anacardium species.

Accordingly the present invention comprises a compound of formula I

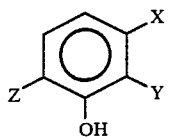

wherein:
X represents a straight chain hydrocarbyl group containing from 8 to 17 carbon atoms;
when Z represents hydrogen, Y represents the group —CH═NOH; and
when Y represents hydrogen, Z represents the group —CH═NOH or —CPh═NOH.

Electronegative substituents, such as chloro, nitro and cyano groups, may also be present on the aromatic ring.

Compounds of formula I are preparable from the carbonyl precursors of the oximes by treatment with appropriate reagents e.g. hydroxylamine salts, typically the hydrochloride or sulphate in a solvent such as anhydrous pyridine or aqueous ethanol with sodium acetate, if necessary or preferred with the application of heat.

The present invention further includes within its scope carbonyl compounds IA which are compounds of formula I in which:
X represents a straight chain hydrocarbyl group containing from 8 to 17 carbon atoms, when Z represents hydrogen, Y represents —CHO and when Y represents hydrogen, Z represents —CHO and —COPh.

Aldehyde precursors for compounds I in which Y represents —CH═NOH may be produced for example from (15:0), (15:1), (15:2) and/or (15:3) anacardic acid IB, which are compounds of formula I in which Z═H, Y═CO₂H and X═C₁₅H₂₅, C₁₅H₂₇, C₁₅H₂₉ or C₁₅H₃₁ by various methods. Such methods include
(1) Reduction e.g. hydride reduction to the corresponding alcohol followed by oxidation thereof to the aldehyde using for example periodate to produce a spirodienone which is subsequently ultraviolet irradiated or using pyridinium chlorochromate or a pyridine/chromium trioxide mixture or
(2) conversion of the acid to the corresponding acid chloride or anhydride or a mixture thereof by treatment with e.g. thionyl chloride followed by reduction of the product to the corresponding aldehyde by means for example of a suitable Rosenmund catalyst and hydrogen or by hydride.

Anacardic acid is available from natural CNSL as a mixture comprising the compounds IB and it may be desirable to partly or fully reduce the $C_{15}$ side chain to produce the 15:1 or 15:0 compound or a mixture of such compounds prior to conversion to the 15:1 or 15:0 oximes. Full or partial reduction may be accomplished by hydrogenation using for example a catalyst of the Raney or Sabatier type or a palladium catalyst whereas partial reduction to the 15:1 acid can be effected by diimide in a solvent such as ethanol, the diimide being generated in situ suitably from hydrazine hydrate and air.

Aldehyde precursors for compounds I wherein Z represents the group —CH═NOH may be produced by oxidation of the corresponding alcohol using for example the reagents hereinbefore described, the alcohol being obtainable by reduction, typically hydride reduction, of the corresponding acid. Such an acid can be produced for example by a Kolbe reaction of cardanol, IC a compound of formula I in which Z═H, Y═H and X═$C_{15}H_{25}$, $C_{15}H_{27}$, $C_{15}H_{29}$ or $C_5H_{31}$, or an alkali metal salt thereof with carbon dioxide.

The present invention also includes within its scope compounds ID of formula I in which Z represents —CO₂H, Y represents hydrogen and X represents a straight chain hydrocarbyl group containing from 8 to 17 carbon atoms.

Alternatively, cardanol (IC) can be formylated to produce a compound comprising a —CHO group at the ring position para to the side chain by treatment with an alkylmagnesium halide e.g. ethyl magnesium bromide to give the phenoxymagnesium halide derivative of cardanol followed by treatment thereof with paraformaldehyde in an aprotic solvent such as hexamethyl phosphoric triamide.

In yet further methods for production of the aldehyde precursors for oximes, mixed cardanol is reacted in aqueous ethanol with sodium or potassium hydroxy and chloroform to give predominantly the aldehyde of formula I in which X═H, Z═CHO and a small proportion in which Z═H, Y═CHO. The p-isomer also produced has alternative uses after separation from the mixture.

Alternatively, interaction of cardanol with paraformaldehyde and an aromatic primary amine affords an aromatic Mannich base regiospecifically which by oxidation to the Schiff's base and hydrolysis of the latter yields the compound of the formula I in which Y═H, Z═CHO.

In a further method for production of aldehyde precursors for oximes of formula I in which Z represents —CH═NOH, cardanol is converted to the phenoxymagnesium halide derivative which is treated with ethylorthoformate in an aprotic solvent such as tetrahydrofuran followed by hydrolysis of the intermediate acetal. In yet further methods for the production of the aldehyde, cardanol, preferably (15:00) cardanol, is formylated by means of the Gattermann reaction, the product containing an impurity 3-pentadecyl-4-formyl phenol, or is subjected to the Hoesch reaction.

Aldehyde precursors for oximes in which the hydrocarbyl chain X contains 8 carbon atoms may be prepared by degradation of the sidechain of mixed cardanol, followed by formylation and oximation as noted above.

The present invention also includes within its scope alcohols from which the hereinbefore described aldehydes may be obtained by oxidation thereof. Such alcohols, IE are compounds of formula I, in which: Z represents —CH$_2$OH when Y represents hydrogen Y represents —CH$_2$OH when Z represents hydrogen and X represents a straight chain hydrocarbyl group containing from 8 to 17 carbon atoms.

Electronegative ring substituents, such as chloro, nitro and cyano groups, enhance the chelation properties of the oxime product. Such substituents may be introduced, by conventional methods, onto the aromatic ring of either the acid or the alcohol. Such substituted acids and alcohols are within the scope of the invention.

Cardanol is obtainable from Technical Cashew Nut-Shell Liquid (CNSL), in which it is present in high concentration, or Technical CNSL may be used per se generally after reduction for example as hereinbefore described for anacardic acid to give compounds containing 15:0 or 15:1 side chains or a mixture comprising such compounds.

Technical CNSL or cardanol may also be used as a starting material for the production of the ketone precursor of compounds I in which Z represents —CPh=NOH. After any desired reduction of the unsaturation in the side chain by methods such as those hereinbefore described, CNSL or Cardanol may be treated with a benzoyl halide, typically benzoyl chloride in the presence of a Lewis acid such as AlCl$_3$ under conditions appropriate for Friedel-Crafts reaction to yield the precursor.

Industrial CNSL is generally dark brown in colour, which may be disadvantageous in some applications, such as for surface coatings. It has been established that the dark brown colour is due to the presence of carbonaceous material, such as tannins, dissolved out from cashew nut shell during extraction of the CNSL, and to the oxidative and thermal degradation compounds of the polyhydric phenols, predominantly cardol, present in the CNSL.

Consequently, it has been desired to provide a method for producing cardanol of high purity. Several methods have been proposed, such as simple vacuum distillation and molecular distillation. The former technique was largely unsuccessful, as polymerisation of all components of the CNSL, including cardanol, tended to occur. Molecular distillation, although quite successful, requires very expensive capital equipment.

More recently, it has been proposed to take advantage of the higher acidity of cardol as compared with cardanol to selectively react cardol to form the monoalkyl ammonium salt, as disclosed in our co-pending application No. 2 066 820. This technique allows up to 70% of the cardol to be removed.

According to the present invention there is also provided a method of separating cardanol from a mixture containing dihydric phenols and cardanol, comprising reacting the dihydric phenols in the mixture with an aldehyde whilst leaving the cardanol substantially unreacted, thereby forming a reacted mixture from which the unreacted cardanol can be separated by distillation. The principal dihydric phenol present in CNSL is cardol which has the formula II.

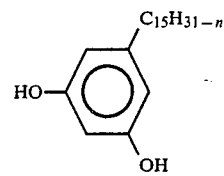

There is further provided according to the invention a method of extracting copper from an acidic aqueous solution containing copper comprising:
treating such a solution with a solution of a compound of the formula I in a water immiscible solvent;
separating the aqueous phase from the water immiscible phase; and
extracting the copper from the water immiscible phase.

Different species of Anacardium yield anacardic acids containing hydrocarbyl side chains of different lengths. For example, an anacardic acid containing a C$_{11}$ side chain may be obtained from the *Anacardium giganteum*, and particularly from the nut-shell of this species.

Extractants of formula I may be utilised for extraction of a metal such as copper by treatment of a solution or dispersion thereof in a water immiscible solvent (typically a non polar solvent such as kerosene), with a mildly acidic aqueous solution of the metal salt e.g. CuSO$_4$ which generally contains salts of other metals uch as nickel. Following agitation of the two phase system to promote extraction into the non-polar phase the phases are separated and the extracted metal salt is stripped therefrom, generally by treatment with an acid e.g. sulphuric acid at a concentration greater than that present in the aqueous phase before extraction e.g. 1.5 molar or stronger sulphuric acid.

The present invention is illustrated by the following Examples:

EXAMPLE 1

(15:0)-Anacardic aldoxime
(6-Pentadecylsalicyladoxime)

(A) 15:0 Anacardic Alcohol

Anacardic acid consisting of a mixture of (15:0), (15:1), (15:2) and (15:3)-anacardic acids is extracted from natural cashew nut-shell liquid as described in Tyman and Lam, J. Chem. Soc., Perkin 1, 1981, 1924 and is obtained as an oil in 69% Yield.

The oil (30 g) in ethyl acetate (200 cm$^3$) containing 10% palladium-carbon catalyst (3.0 g) is shaken with hydrogen at 15lb in$^{-2}$ at ambient temperature. After absorption of hydrogen (3,530 cm$^3$) the reduction is complete. The mixture is filtered to recover the catalyst and upon evaporation and recovery of the solvent, (15:0)-anacardic acid obtained in theoretical yield, m.p. 87°–88°.

(15:0)-Anacardic acid (5.2 g) in dry tetrahydrofuran (60 cm$^3$) is added dropwise over two hours to lithium aluminium hydride (2.5 g) suspended in tetrahydrofuran (25 cm$^3$) and the stirred mixture is refluxed for two hours with monitoring by thin layer chromatography to indicate complete reduction. The excess hydride is decomposed by the addition of ethyl acetate and the acidified mixture is extracted with ether. Recovery gives a brown oil which upon crystallization from light petroleum (40°–60°) yields (15:0)-anacardic alcohol (6-pentadecylsalicyl alcohol) as cream coloured crystals, m.p. 60°–62° (4.05 g).

(B) 15:0 Anacardic Aldehyde (15:0)-Anacardic alcohol (2.0 g) in methanol (30 cm$^3$) is reated with a solution of sodium periodate (1.76 g) in water (10 cm$^3$). After several minutes a thick yellow solid separates and the stirred mixture is warmed at 30° C. for one hour to complete the reaction. Dilution with water and ethereal extraction gives a thick yellow oil which after crystallization from light petroleum (40°–60°) affords the spirodienone, 8-pentadecyl-1-oxaspiro (2.5) octa-5, 7-dien-4-one, m.p. 80°–81° C. (1.20 g).

The spirodienone (1.08 g) in ethanol is irradiated with ultra-violet light from a medium pressure Hanovia photochemical reactor during three hours. Concentration of the solution, ethereal extraction and crystallisation from light petroleum (40°–60°) gives pale yellow crystals of (15:0)-anacardic aldehyde (6-pentadecylsalicylaldehyde), m.p. 45°–47° (1.01 g).

(C) 15:0 Anacardic aldoxime (15:0)-Anacardic aldehyde (0.41 g) in pyridine (7 cm$^3$) is heated at 100° C. with hydroxylamine hydrochloride (0.746 g). Oximation is complete after five hours and the mixture is diluted with water, acidified with hydrochloric acid and ethereally extracted. Concentration of the dried ethereal solution gives a greyish oil which after crystallization from light petroleum (40°–60°) furnished (15:0)-anacardic aldoxime as off-white prisms, m.p. 95°–97°, (0.34 g).

Found: C, 75.45; H, 10.77; N, 3.80. $C_{22}H_{37}O_2N$ requires C, 76.08; H, 10.66; N, 4.03%.

It had the expected $^1H$ NMR and IR absorption spectra.

EXAMPLE 2

15:0 Anacardic aldoxime

The oxime is produced as described in Example 1 from 15:0 Anacardic aldehyde produced by a procedure in which oxidation of (15:0)-anacardic alcohol (2.0 g) in dichloromethane (110 cm$^3$) with pyridinium chlorochromate (5.50 g), prepared from chromium trioxide and 6M hydrochloric acid, is followed by addition at 0° of pyridine according to Corey and Suggs (Tetrahedron Letters, 1975, 2647), during 90 minutes at ambient temperature. Filtration of the reaction mixture, concentration of the filtrate and crystallisation gives (15:0)-anacardic aldehyde identical with the product from the process described in Example 1.

EXAMPLE 3

(A) 15:0 Anacardic aldehyde (15:0)-Anacardic acid (3.48 g) in light petroleium, 40°–60° C. (20 cm$^3$) containing pyridine (0.02 g) is stirred and treated with thionyl chloride (0.62 cm$^3$) at 30°. After two hours the mixture which becomes almost clear is filtered and the filtrate concentrated to give an oily product consisting of the acid chloride and the acid anhydride.

The crude product from two such reactions (5 g) in dry xylene (9.2 cm$^3$) containing 5%-palladium barium sulphate catalyst (0.27 g) and thiourea, catalyst poison, (0.055 g) is heated at 140°–150° and hydrogen passed into the mixture with the usual precautions. Hydrogen chloride soon appears in the exit gas and is collected in a water trap. When no more is produced the reaction is stopped, the reaction mixture is cooled, decolourising charcoal (1 g) added and after filtration and concentration the residual material (4.60 g) is crystallised from light petroleum (40°–60°) to give (15:0)-anacardic aldehyde which is identical with the products from the reactions described in Examples 1 and 2.

(B) 15:0 Anacardic aldoxime

The aldehyde is converted into the corresponding aldoxime as described in Example 1.

EXAMPLE 4

(A) 15:0 Anacardic aldehyde

A mixture of acid chloride and anhydride produced as described in Example 3 (1.0 g), is reduced in diglyme (1.1 cm$^3$) at −75° C. with a t-butanol/lithium aluminium hydride complex, obtained by reacting dry t-butanol (0.6 g) with lithium aluminium hydride (0.106 g) in dry ether (5.6 cm$^3$) and dissolving the precipitate in diglyme (2.2 cm$^3$), to give (15:0)-anacardic aldehyde which is purified by crystallisation to give (0.69 g).

(B) 15:0 Anacardic aldoxime is produced from the aldehyde as described in Example 1.

EXAMPLE 5

4-Pentadecylsalicylaldoxime ("(15:0)-iso-anacardic aldoxime")

(A) 4-Pentadecylslicylic acid

The unsaturated product "iso-anacardic acid" 4-pentadecylsalicylic acid from the Kolbe reaction of the sodium salt of cardanol with carbon dioxide is hydrogenated to give the saturated compound in the following manner.

The unsaturated acid, consisting of (15:0), (15:1), (15:2) and (15:3) constituents (20 g) in ethanol (150 cm$^3$) containg 10% palladium-carbon catalyst (2.0 g) is hydrogenated until 2500 cm$^3$ of hydrogen has been absorbed. Filtration to recover the catalyst and concentration of the filtrate followed by crystallisation of the residual material gives 4-pentadecylsalicylic acid, (15:0)-iso-anacardic acid as greyish prisms, m.p. 96°–97° (14.8 g).

(B) 4-Pentadecylsalicyl alcohol

4-Pentadecylsalicylic acid (5.3 g) in dry tetrahydrofuran (60 cm$^3$) is slowly added to stirred lithium aluminium hydride (2.5 g) in dry tetrahydrofuran (25 cm$^3$) and the mixture then stirred and refluxed for five hours to complete the reduction. Work-up by recovery of the tetrahydrofuran, addition of a little ethyl acetate to the cooled residual material, followed by acidifiction and ethereal extraction yields the crude product which is crystallised from light petroleum (40°–60°) to give 4-pentadecylsalicyl alcohol as pale cream prisms, m.p. 94°–95°, (4.05 g).

Analysis of the product showed that it contained a C; 78.9%, H 11.55% 4-pentadecylsalicyl alcohol, $C_{22}H_{38}O$, requires C 79.0% H 11.40%.

(C) 4-Pentadecylsalicylaldehyde

4-Pentadecylsalicyl alcohol (1.54 g) in methanol (25 cm$^3$) is treated with sodium periodate (1.30 g) in water (8 cm$^3$). A thick yellow solid soon separates and the mixture is warmed to 30° during five hours to complete the reaction, which is indicated by monitoring with thin layer chromatography. Dilution of the mixture with water and ethereal extraction followed by concentration of the ethereal layer and crystallisation of the residue from light petroleum (40°-60°) affords the "isomeric spiro epoxy dienone", m.p. 84°-86° C., (0.82 g).

Irradiation of the spirodienone (0.72 g) in ethanol with ultraviolet light in an Hanovia photochemical reactor during three hours and recovery and crystallisation of the product from light petroleum (40°-60°) gives 4-pentadecylsalicylaldehyde as a pale yellow material, m.p. 50°-54°, (0.61 g).

(D) 4-Pentadecylsalicylaldoxime

Interaction of the aldehyde in pyridine solution with hydroxylamine hydrochloride at 100° during five hours yields 4-pentadecylsalicyladoxime, "15:0)-isoanacardic aldoxime".

EXAMPLE 6

(A) 4-Pentadecylsalicylaldehyde

Cardanol consisting of a mixture of (15:0)-cardanol, (15:1)-cardanol, (15:2)-cardanol and (15:3)-cardanol is obtained from the technical cashew nut-shell liquid by vacuum distillation in 70% yield.

The mixed material in ethanol containing 10% palladium-carbon catalyst is hydrogenated until absorption of hydrogen ceased and the side-chain has been saturated as revealed by argentation thin layer chromatography and $^1$H NMR absorption spectroscopy. The product is recovered by filtration, concentration of the filtrate and crystallisation of the residual material from light petroleum (40°-60°) to give (15:0)-cardanol, containing a little (15:0)-cardol.

Alternatively the mixed cardanol can be chemically reduced with hydrazine and an air in aqueous ethanolic solution to give (15:0) cardanol.

(15:0)-Cardanol (10.2 g) is added to an equivalent proportion of ethyl magnesium bromide in dry ethereal solution to form the phenoxy magnesium bromide, completion of which is observed when evolution of ethane ceases. Ethyl orthoformate (10 cm$^3$) is added and the ether removed by distillation so that the temperature rises to 100° C. After refluxing for three hours, the mixture is decomposed with dilute hydrochloric acid and warmed to effect the hydrolysis of the intermediate acetal formed. Etheral extraction and recovery gives a mixture of some unchanged (15:0)-cardanol and the formylated product, 4-pentadecylsalicylaldehyde which is separated by chromatography.

(B) 4-Pentadecylsalicylaldoxime

The aldehyde is converted into the corresponding aldoxime by the process described in Example 5.

EXAMPLE 7

(A) 4-Pentadecylsalicylaldehyde (15:0)-cardanol constituents (2.0 g) is converted as described in Example 6 to the phenoxy magnesium bromide derivative and refluxed in benezene (50 cm$^3$) containing hexamethyl phosphoric triamide (1.2 g) and paraformaldehyde (0.67 g) for three hours. Acidification and ethereal extraction followed by drying and concentration gives a pale brown oil consisting of some unchanged (15:0)-cardanol and 4-pentadecylsalicylaldehyde which are separated by crystallisation or flash chromatography. Almost none of the 6-pentadecyl isomer is present.

(B) 4-Pentadecylsalicylaldoxime

The aldehyde is converted into the corresponding aldoxime by the process described in Example 5.

EXAMPLE 8

Mixed (15:0), (15:1), (15:2) and (15:3) isoanacardic aldoxime

Mixed cardanol (6.0 g) in dry ether (50 cm$^3$) is treated with an ethereal solution of ethyl magnesium bromide prepared from magnesium (0.5 g) and bromoethane (2.21 g) in dry ether (50 cm$^3$) and the mixture heated to complete the reaction. The ether is distilled and replaced by dry benzene (100 cm$^3$) to effect complete recovery of the ether. Hexamethyl phosphoric triamide (4.2 cm$^3$) and a suspension of paraformaldehyde (1.53 g) in dry benzene (80 cm$^3$) are then added and the solution is refluxed for 3½ hours. Further paraformaldehyde (0.76 g) is added to replenish that lost by sublimation and after further refluxing the mixture is worked up, the whole process having been monitored by TLC and $^1$H NMR spectroscopy. The cooled mixture is treated with dilute hydrochloric acid thoroughly agitated and the benzene layer is removed, dried and filtered. The filtrate, after washing with water, is concentrated to dry the product and recover the benzene. The residual oil consists substantially of the mixed constituents of isoanacardic aldehyde with only a small amount of the 6-isomer and cardanol present. Upon purification by flash chromatography, iso-anacardic aldehyde (5.24 g, 78%) was obtained, containing some 6-isomer. The product had the expected $R_f$(by TLC), IR and $^1$H HNR absorption and contained a small proportion of unchanged cardanol.

EXAMPLE 9

(15:0), (15:1), (15:2) and (15:3) iso-Anacardic and Anacardic aldehydes

A product containing both anarcardic and isoanacardic aldehydes can be obtained by the reaction of mixed cardanol in aqueous ethanol containing sodium and potassium hydroxide with chloroform.

EXAMPLE 10

(15:0), (15:1), (15:2) and (15:3) iso-Anacardic aldehyde

Mixed cardanol (3.79 g), p-toluidine (1.30 g), paraformaldehyde (0.45 g) and anhydrous sodium carbonate (0.30 g) are stirred in water (9 cm$^3$) for 2½ hours at 60° C. Toluene (5 cm$^3$) is added and stirring continued for 5 hours. The toluene layer is separated and ferric sulphate (6.20 g) in water (8 cm$^3$) added the mixture being stirred for 17½ hours. The toluene layer is then removed and refluxed with dilute sulphuric acid from concentrated sulphuric acid (2.5 cm$^3$) in water (4.5 cm$^3$) for 4 hours. The toluene layer is then washed over with water until neutral, dried and evaporated to give a brown oil (2.44 g). This is purified by vacuum distillation or by 'flash' chromatography to give iso-anacardic aldehyde (0.87 g) and unchanged cardanol (0.56 g).

EXAMPLE 11

2-Hydroxy-4-pentadecyl benzophenone ketoxime (A) 2-hydroxy-4-pentadecylbenzophenone (15:0)-Cardanol (2.0 g) in dry pyridine (5 cm$^3$) is treated with benzoyl chloride (1.5 cm$^3$) and the mixture warmed for five hours at 100° C. The cooled mixture is diluted with water, basified with dilute sodium hydroxide solution, and the pecipitated (15:0)-cardanol benzoate collected by filtration, washed with water until neutral and dried to give 2.785 g.

3-Pentadecylphenyl benzoate (1.366 g) is finely powered, mixed with pulverised anhydrous aluminium chloride (0.616 g) and the intimate miture is heated to 165° during fifteen minutes. After hydrogen chloride evolution has ceased, the cooled mixture is treated with water, concentrated hydrochloric acid added, and the whole thoroughly stirred to decompose the aluminium complex. The product is ethereally extracted and the dried ethereal layer is concentrated to give the crude product (1.348 g) which possesses a greenish ferric chloride reaction. Chromatographic purification and crystallisation from light petroleum (40°-60°) afford 2-hydroxy-4-pentadecylbenzophenone, m.p. 46°-47°.

(B) 2-hydroxy-4-pentadecyl benzophenone ketoxime

Conversion to 2-hydro-4-pentadecylbenzophenone oxime is effected in pyridine solution with hydroxylamine hydrochloride as described in Example 1 or 5 to give the product, m.p. 51°-3° C.

EXAMPLE 12

The extraction properties of (15:0)-anacardic aldoxime for copper ions are compared with those of the commercial extractant, the oxime of 2-acetyl-4-nonyl phenol (SME 529). The following solutions are used.

A Standard copper sulphate solution, 5.715 g/liter of $CuSO_4 \cdot 5H_2O$

B Anacardic aldoxime, 1.25% w/w, $3.6 \times 10^{-3}$ moles/100 $cm^3$ of petroleum (100–120)

C 2-Acetyl-4-nonyl phenolketoxime, 1.25% w/w, $4.5 \times 10^{-3}$ moles/100 $cm^3$ of petroleum (100°-120°)

D 1.50M aqueous sulphuric acid

Solution B (20 $cm^3$) is thoroughly mixed with Solution A (10 $cm^3$) and similarly Solution C (20 $cm^3$) is mixed with Solution A (10 $cm^3$). Excess of copper ion is present to ensure, if possible, maximum loading of oxime compounds. The pH was 5. Both solutions are thoroughly shaken and after emulsion separation has occurred, the lower copper sulphate aqueous layer is removed and analysed for copper sulphate by iodometric titration. The following results at the extraction stage are obtained on the basis that 1 g atom of copper is associated with 2 moles of the oxime derivative. Each of the organic solutions are finally washed with Solution D (2×10 $cm^3$) to recover the copper extracted.

|  | Anacardic Aldoxime | 2-acetyl-4-nonyl phenolketoxime |
|---|---|---|
| Moles of reagent oxime used | $7.20 \times 10^{-4}$ | $9.00 \times 10^{-4}$ |
| Equivalent to moles copper | $3.60 \times 10^{-4}$ | $4.50 \times 10^{-4}$ |
| Equivalent to g copper | $2.29 \times 10^{-2}$ | $2.86 \times 10^{-2}$ |
| Max. theoretical loading | $2.29 \times 10^{-2}$ | $2.86 \times 10^{-2}$ |
| Copper extracted (g) | $2.33 \times 10^{-2}$ | $1.27 \times 10^{-2}$ |
| Copper initally present (g) | $5.715 \times 10^{-2}$ | $5.715 \times 10^{-2}$ |
| % copper extracted | 40.7 | 22.2 |
| % theoretical loading of copper | 100 | 44.4 |
| % recovery of copper | 91 | 100 |

Both reagents are stable to the acidic conditions of recovery as assessed by thin layer chromatography.

EXAMPLE 13

The extraction properties of mixed iso-anacardic aldoxime (S), containing some anacardic aldoxime, both of which conist of (15:0), (15:1), (15:2) and (15:3) constituents were compared with those of three commercial extractants: 2-formyl-4-nonylphenol ketoxime (A) 2-acetyl 4-nonyphenol ketoxime (B); and 2-benzoyl-4-nonylphenol ketoxime (C).

10% solutions were made in petroleum (100°-120°). It was found that, with excess reagent present, the relative removal of the available copper from 10 $cm^3$ of copper sulphate solution containing $6.5 \times 10^{-3}$ g $Cu^{++}/cm^3$ was as is shown in the first column in the table below, and, upon stripping, in the second column.

In a second comparative experiment, the results are the stripping stage were as is shown in the third column of the table.

| Extractant | 1st Comparative Experiment | | 2nd Comparative Experiment Stripping (%) |
|---|---|---|---|
| | Extraction (%) | 1st Stripping (%) | |
| S | 95 | 87 | 93 |
| A | 87 | 96 | 97 |
| B | 60 | 100 | 100 |
| C | 54 | 100 | 100 |

The addition of mixed cardanol improved the rate of separation of the organic and aqueous phases after the agitation. Upon addition of excess copper, the extractant removes the stoichimetric amount of copper. 1 mole of extractant S removes 0.5 mole copper from solution.

EXAMPLE 14

In an extraction process similar to that of Example 9 in which nickel chloride is present which copper sulphate in equimolar strength, analysis by atomic absorption indicates that anacardic aldoxime (like the ketoxime reagent) extracts copper specifically.

Turning now to the method of separating cardanol from a mixture containing dihydric phenols and cardanol, this will now be described with reference to the separation of cardanol from CNSL.

It has been found that a particularly advantageous result may be achieved by subjecting CNSL to a Mannich type reaction. The Mannich reaction involves reacting the substrate with an aldehyde, such as formaldehyde, and a primary or secondary amine. Under these conditions, it has been found that while the dihydric phenol cardol forms a high molecular weight reaction product, the monohydric phenol cardanol remains substantially unreacted. The cardanol may then be removed from the reaction by working up followed by vacuum distillation.

The most preferred amines are diethylenetriamine (DETA) and n-butylamine, and it is preferred to carry out the reaction in methanolic solution. While it is uncertain what reactions occur, and while not wishing to be bound by any theoretical explanations, the following reactions are postulated.

With diethylenetriamine:

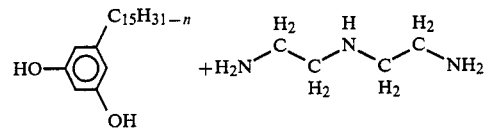

-continued

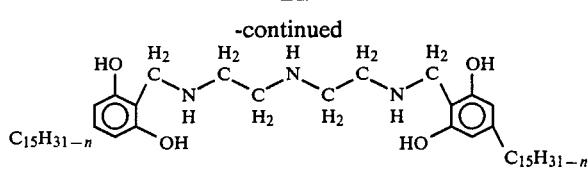

where n=0, 2, 4, 6.
With n-butylamine:

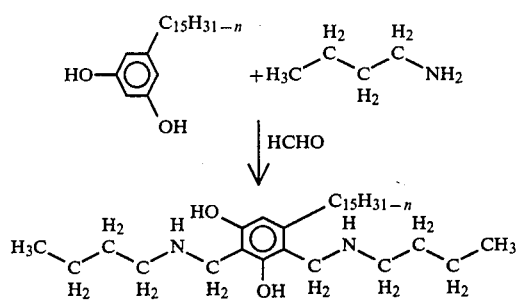

where n=0, 2, 4, 6.

With diethylenetriamine (DETA), the following reaction conditions are found to be advantageous:

The molar proportions of reactants, CNSL, DETA, and formaldehyde found particularly useful are CNSL (1 mol), DETA (0.125 mol), formaldehyde (1.20 mol). (The average mol. wt. of technical CNSL is taken to be 300). Formaldehyde as 40% w/v aqueous solution is preferred.

If the formaldehyde is reduced to 0.6 mol or even 0.3 mol the proportion of cardol in the reaction drops more slowly. Therefore, formaldehyde in the range of 1.0 to 1.2 mol is preferred. The DETA is preferably used in approximately molar proportion to the cardol present in the technical CNSL. If the DETA proportion is dropped below 0.125 mol/mol CNSL, then removal of cardol is slower.

The proportion (volume) of methanol preferred is 1 l/mol CNSL. If less is used, phase separation becomes less easy. The methanol may be added at the end of the reaction of the CNSL, DETA and formaldehyde.

The temperature of the reaction is usually ambient, although it will take place down to 0° C. Temperatures above ambient are not required and indeed since the reaction is slightly exothermic some cooling is desirable in large batches.

With n-butylamine, the following reaction conditions are found to be advantageous:

The molar proportions of reactants found particularly useful are CNSL (1 mol), n-butylamine (0.183 mol), formaldehyde (1.20 mol). With these proportions it was established on a small scale that at least 97.2% of the cardanol was recovered.

If the formaldehyde is reduced, the removal of cardol from CNSL becomes slower. Formaldehyde in the range 1.0 to 1.2 mol/mol CNSL is preferred. The proportion of n-butylamine used is preferably related to the amount of cardol present in the CNSL.

If the volume of methanol is reduced below 1 liter/mol of CNSL, for example to half volume, the phase separation becomes more difficult.

Reaction at lower temperatures, for example at 0° C., may result in a less effective removal of cardol. Thus ambient temperature is preferred. For large scale reactions cooling of the mixture is desirable.

By way of illustration, the following examples are offered.

EXAMPLE 5

Technical CNSL (60 g), 40% formaldehyde solution (19.4 g) and diethylenetriamine (2.57 g) were mixed in methanol (200 cm$^3$). An exothermic reaction took place after mixing the reactants and after thirty minutes a phase separation occurred into an upper, slightly reddish, solution and a lower phase which solidified and was dark in colour. The upper phase was decanted and treated with water (40 cm$^3$) followed by petroleum ether. The petroleum ether extract was distilled to recover the hydrocarbon solvent leaving a reddish residue (36.13 g) which from TLC and HPLC contained cardanol, no cardol, and a small amount of some polar material. Methanol was recovered from the aqueous layer by distillation. The lower solidified phase which was gel-like (25.65) was readily removed from the flask. Distillation of the crude cardanol (36.13 g) gave three fractions; fraction 1, 3.34 g, b.p. up to 160° C./0.11 mm Hg, fraction 2, b.p. 160°–180° C., 11.25 g, fraction 3, b.p. 180°–220° C. 13.73 g. The total yield was 28.32 g (78.4% of the crude cardanol used) and the residue was 7.8 g, 21.6%.

EXAMPLE 16

In a Mannich experiment, technical CNSL (240 g), diethylenetriamine (10.30 g) and 40% formaldehyde solution (77.76 g) were mixed in methanol (800 cm$^3$). The mixture was processed to give crude cardanol (138.0 g; 57.5%). The lower solidified layer was processed separately. Distillation of the crude cardanol gave good cardanol (90.3 g), representing 60.7% of the available cardanol, the fractions having the analyses shown in the Table.

EXAMPLE 17

Technical CNSL (240 g) reacted under the same conditions as in Example 16 gave crude cardanol (125.45 g; 51.85%) and a lower layer (154.58 g). Distillation of the crude cardanol afforded good quality cardanol (100.44 g) representing 67.5% of the available cardanol.

EXAMPLE 18

In a Mannich experiment, technical CNSL (360 g), diethylenetriamine (15.14 g) and 40% formaldehyde solution (116.64 g) were mixed in methanol (1500 cm$^3$). The reaction mixture was processed as in Example 15 to give crude cardanol (181.75 g; 50.5%). The lower solidified phase (227.4 g; 46.2%) was easily removable from the flask. Distillation of the crude cardanol (176.76 g) gave good cardanol (116.27 g) representing 52.1% of the available cardanol as shown in the Table.

EXAMPLE 19

Technical CNSL (60.0 g), 40% formaldehyde solution (19.4 g) and n-butylamine (2.68 g) were mixed in methanol (200 cm$^3$). The reaction proceeded in the same way as in Example 15 and by the use of the same extraction procedure the crude cardanol recovered was 38.38 g which from TLC and HPLC analysis was free from cardol and contained a small amount of polar material. Upon distillation three fractions were obtained as before; fraction 1, 1.09 g fraction 2, 14.97 g and fraction 3, 10.55 g. The total recovery was 26.1 g.

In Examples 15 to 19 the technical CNSL contained cardanol 62.0%, cardol and 2-methylcardol 18.6% and polymeric material 19.4%. The recovery of cardanol based on that in the technical CNSL used was 76% for Example 15 and 70% for Example 16.

A second advantageous process has been developed in which CNSL is reacted with aqueous methanolic formaldehyde in the presence of a small amount of dilute mineral acid. Again, the cardol in the CNSL is polymerised, and the cardanol is substantially unreacted. The reaction is followed by conventional working up and vacuum distillation. Good yields of high purity cardanol are obtained.

Again, the precise reactions occurring are not fully known. While not wishing to be bound by theoretical explanations, the following reaction is postulated:

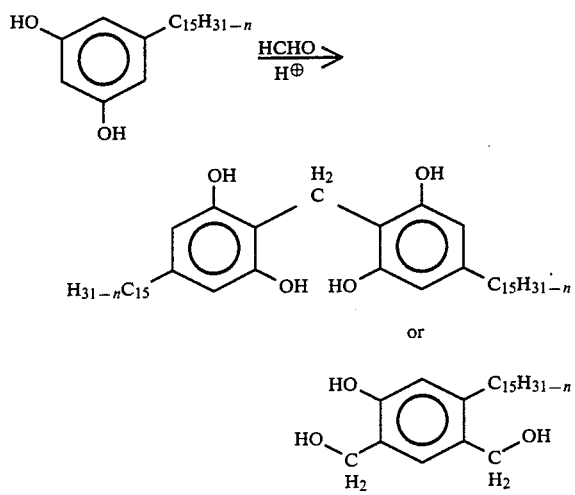

where n=0, 2, 4, 6.

With formaldehyde, the following reaction conditions are found advantageous.

The molar proportions preferred in this purification procedure are CNSL (1 mol) and formaldehyde (0.85 mol).

In the absence of added mineral acid, reaction virtually does not occur. Hydrochloric acid has been used and generally adjustment of the pH to 1 is most favourable. Formaldehyde in the form of formaldehyde solution is used and paraformaldehyde has not been found suitable.

If the molar proportion of formaldehyde is reduced to half, the reaction of cardol is reduced. When 0.17 mol proportion of formaldehyde/mol CNSL is used, 46% of the cardol is unreacted, and with 0.51 molmol CNSL, 23% remains unreacted.

600 $cm^3$ methanol/mol CNSL is preferred. More methanol can be used but generally the use of less than 600 $cm^3$/mol can lead to a faster reaction and careful control by TLC monitoring is then necessary.

Although 40° C. is the preferred temperature on the small scale, on a larger scale careful temperature control is desirable and we have found that cooling to keep the temperature at 40° C. is advantageous.

By way of illustration, the following example is offered:

EXAMPLE 20

Technical CNSL (300 g) and 40% aqueous formaldehyde solution (68.74 g) were mixed in methanol (600 $cm^3$), concentrated hydrochloric acid (5 $cm^3$) was added to adjust the pH to 1 and the mixture was warmed to and held at 40° C. for two and a quarter hours. The product was processed as in Example 15 to give crude cardanol (262.08 g; 87.4%). This material (102.08 g) was vacuum distilled to give two fractions completely free from cardol (totalling 50.87 g; 49.8%). A small final fraction (3.9 g) contains a little cardol. The residue which was easily soluble in chloroform was 40 g (40.07%). The remaining crude cardanol (160.0 g) gave upon vacuum distillation 97.3 g in three fractions. The total recovery of good cardanol from the experiment was 152.1 g (50.7% of the technical CNSL used, and 81.8% of the estimated cardanol present). The results are shown in the Table.

The composition of the distilled reaction products from Examples 15, 18 and 20 are shown in the Table.

A control consisting of the vacuum distillation of technical CNSL without prior Mannich reaction or formaldehyde reaction treatment is also shown in the Table. Although a recovery of cardanol (79.31%) was obtained the analytical figures show that all three fractions contains cardol varying between 8.2% and 19.9%. Material of this type darkened upon storage.

A comparison experiment is also shown in the Table of an amine/salt procedure. In this experiment, technical CNSL (200 g) and 40% aqueous tetra n-butylammonium hydroxide (105 $cm^3$) were placed together and after several days the mixture was heated to dehydrate it and 50 g of the resultant mixture was vacuum distilled. Three fractions were obtained as shown in the Table. Although the total recovery is quite good all the fractions contained some cardol, although this was les than in the absence of the base.

Methods according to the invention provide a means of effectively separating cardanol from the other components of CNSL in better yields than have been obtained with previously known methods, and at lower cost by molecular distillation techniques. Further, the residue remaining after distillation of cardanol from the reaction mixture may be easily removed by, for example, dissolution in chloroform.

TABLE

| Example | Weight Distilled | Fractions (g) | b.p. °C./mm Hg | % Composition (from HPLC Analysis) | | | | | | Total Recovery (g) | Total Residue (g) |
| --- | --- | --- | --- | --- | --- | --- | --- | --- | --- | --- | --- |
| | | | | Cardol | | Cardanol | | | | | |
| | | | | 15:3 | 15:2 | 15:3 | 15:2 | 15:1 | 15:0 | | |
| 16 | 138.0 | (1) 5.48 | 180/0.1 | — | — | — | — | — | — | | |
| | | (2) 70.17 | 180–190/0.1 | — | — | 52.41 | 18.18 | 26.59 | 2.82 | 90.03 | 36.09 |
| | | (3) 14.38 | 200–250/0.1 | 4.1 | — | 51.90 | 16.00 | 23.77 | 3.21 | (65.23%) | (26.10%) |
| 18 | 176.72 | (1) 21.67 | 180/0.06 | — | — | 49.24 | 19.61 | 28.33 | 2.67 | | |
| | | (2) 76.27 | 180–190/0.06 | — | — | 56.83 | 15.25 | 24.83 | 2.78 | 116.27 | 58.49 |
| | | (3) 18.33 | 190–220/0.06 | 1.69 | — | 53.3 | 16.41 | 24.29 | 3.19 | (65.79%) | (33.09%) |
| 20 | 102.08 | (1) 2.57 | 180/0.06 | — | — | 50.45 | 18.37 | 28.56 | 2.51 | 50.87 | 40 |
| | | (2) 48.30 | 180–190/0.06 | 1.37 | — | 50.72 | 17.59 | 27.13 | 3.18 | (49.8%) | (40.07%) |

TABLE-continued

| Example | Weight Distilled | Fractions (g) | b.p. °C./mm Hg | % Composition (from HPLC Analysis) | | | | | | Total Recovery (g) | Total Residue (g) |
| --- | --- | --- | --- | --- | --- | --- | --- | --- | --- | --- | --- |
| | | | | Cardol | | Cardanol | | | | | |
| | | | | 15:3 | 15:2 | 15:3 | 15:2 | 15:1 | 15:0 | | |
| Control | 158.89 | (1) 10.81 | 180/0.1 | 6.05 | 2.13 | 47.75 | 15.90 | 25.11 | 2.80 | 126.02 | 30.64 |
| | | (2) 92.26 | 180–190/0.1 | 7.63 | 2.27 | 46.58 | 16.73 | 24.78 | 2.66 | (79.31%) | (19.28%) |
| | | (3) 22.95 | 190–210/0.1 | 15.11 | 4.83 | 41.15 | 15.73 | 20.05 | 2.64 | | |
| Amine/ | | (1) 8.5 | 165–173/0.1 | | 7.2 | 43.1 | 20.2 | 36.7 | — | | |
| CNSL | | (2) 6.5 | 173–200/0.1 | | 7.4 | 43.6 | 20.6 | 35.7 | — | | |
| method | | (3) 14.6 | 200–220/0.1 | | 10.8 | 47.1 | 22.2 | 30.7 | — | | |
| | | (residue 6.8 g) | | | | | | | | | |

What is claimed is:

1. A compound useful for extraction of copper from acidic media of the formula

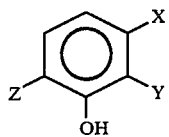

in which:
X represents a straight chain hydrocarbyl group containing from 8 to 17 carbon atoms,
Y represents H or the group —CH=NOH, and
Z represents H or the group —CH=NOH,
provided that Y and Z are different; or such compound containing at least one electronegative substituent on the aromatic ring selected from the group consisting of chloro, nitro and cyano.

2. The compound of claim 1, wherein Y is the group —CH=NOH and Z is H.

3. The compound of claim 1, wherein Z is the group —CH=NOH and Y is H.

4. The compound of claim 1, wherein X is a pentadecyl group.

5. The compound of claim 1, which is 6-pentadecyl salicylaldoxime.

6. The compound of claim 1, which is 4-pentadecylsalicylaldoxime.

7. A compound of the formula

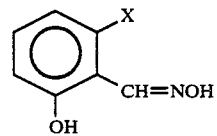

wherein X is a straight chain hydrocarbyl group containing from 8 to 17 carbon atoms.

8. A compound of the formula

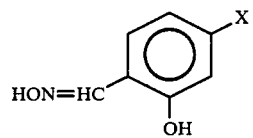

wherein X is a straight chain hydrocarbyl group containing from 8 to 17 carbon atoms.

* * * * *

UNITED STATES PATENT AND TRADEMARK OFFICE
CERTIFICATE OF CORRECTION

PATENT NO. : 4,697,038
DATED : Sep. 29, 1987
INVENTOR(S) : Tyman

It is certified that error appears in the above-identified patent and that said Letters Patent is hereby corrected as shown below:

On the Title Page:

In the category "[73] Assignee:" change "501 Brunel University, Middlesex, England" to --Brunel University, Middlesex, England--.

Signed and Sealed this

Twentieth Day of September, 1988

Attest:

DONALD J. QUIGG

*Attesting Officer*  *Commissioner of Patents and Trademarks*